US009119842B2

United States Patent
Takemoto et al.

(10) Patent No.: US 9,119,842 B2
(45) Date of Patent: Sep. 1, 2015

(54) THERAPEUTIC MESO-BILIVERDIN IXα COMPOSITIONS AND ASSOCIATED METHODS

(71) Applicants: Jon Y. Takemoto, North Logan, UT (US); Dong Chen, Logan, UT (US); Cheng-Wei T. Chang, Logan, UT (US); Jonathan Wood, North Logan, UT (US)

(72) Inventors: Jon Y. Takemoto, North Logan, UT (US); Dong Chen, Logan, UT (US); Cheng-Wei T. Chang, Logan, UT (US); Jonathan Wood, North Logan, UT (US)

(73) Assignee: Utah State University, North Logan, UT (US)

( * ) Notice: Subject to any disclaimer, the term of this patent is extended or adjusted under 35 U.S.C. 154(b) by 0 days.

(21) Appl. No.: 14/028,313

(22) Filed: Sep. 16, 2013

(65) Prior Publication Data

US 2014/0079723 A1   Mar. 20, 2014

Related U.S. Application Data

(60) Provisional application No. 61/701,465, filed on Sep. 14, 2012.

(51) Int. Cl.
*A61K 31/409* (2006.01)
*A61K 45/06* (2006.01)

(52) U.S. Cl.
CPC .............. *A61K 31/409* (2013.01); *A61K 45/06* (2013.01)

(58) Field of Classification Search
IPC .................................................... A61K 31/409
See application file for complete search history.

(56) References Cited

U.S. PATENT DOCUMENTS

| | | | |
|---|---|---|---|
| 5,624,811 | A | 4/1997 | Lang et al. |
| 6,689,578 | B2 | 2/2004 | DeZwaan et al. |
| 6,969,610 | B2 | 11/2005 | Maines |
| 7,504,243 | B2 | 3/2009 | Pendrak |
| 8,097,585 | B2 | 1/2012 | Bach et al. |
| 8,344,019 | B2 | 1/2013 | Pendrak et al. |
| 8,455,222 | B2 | 6/2013 | Takemoto et al. |
| 2003/0027124 | A1 | 2/2003 | Maines |
| 2005/0209305 | A1 | 9/2005 | Pendrak et al. |
| 2006/0110827 | A1 | 5/2006 | Lagarias et al. |
| 2009/0169586 | A1* | 7/2009 | Tracton ........................ 424/400 |
| 2009/0203762 | A1 | 8/2009 | Pendrak et al. |
| 2011/0104728 | A1 | 5/2011 | Takemoto et al. |
| 2011/0217764 | A1 | 9/2011 | Christenson et al. |
| 2012/0142751 | A1 | 6/2012 | Pendrak et al. |
| 2013/0096318 | A1 | 4/2013 | Takemoto et al. |

FOREIGN PATENT DOCUMENTS

| | | |
|---|---|---|
| WO | 0196345 A1 | 12/2001 |
| WO | 2009054150 A1 | 4/2009 |
| WO | 2011002584 A1 | 1/2011 |

OTHER PUBLICATIONS

Wedemayer et al., "Phycobilins of cryptophycean algae," J Biol Chem 267(11):7315-7331, 1992.*

(Continued)

*Primary Examiner* — Rosanne Kosson

(57) ABSTRACT

Methods and materials for treating various diseases and medical conditions with meso-biliverdin compositions. In addition methods and materials for producing meso-biliverdin are provided where the methods include reacting phycocyanobilin with an amphoteric compound in a solvent to yield meso-biliverdin are provided.

17 Claims, 3 Drawing Sheets

(56) References Cited

OTHER PUBLICATIONS

Ding et al., "The Coordinated Increased Expression of Biliverdin Reductase and Heme Oygenase-2 Promotes Cardiomyocyte Survival: a Reductase-Based Peptide Counters B-Adrenergic Receptor Ligand-Mediated Cardiac Dysfinction", The FASEB Journal, Sep. 27, 2010, vol. 25, p. 1-13, FASEB, Bethesda, MD.

Hoare & Datta, "Characteristics of L-Alanine: 4, 5-Dioxovaleric Acid Transaminase: An Alternate Pathway of Herne Biosynthesis in Yeast", Archives of Biochemistry and Biophysics, Feb. 15, 1990, vol. 227, No. 1, p. 122-129, Elsevier, Cambridge, MA.

Kapitulnik & Maines, "Pleiotropic Functions of Biliverdin Reductase: Cellular Signaling and Generation of Cytoprotective and Cytotoxic Bilirubin", Trends in Pharmacological Sciences, Mar. 2009, vol. 30, Issue 3, p. 129-137, Elsevier, Cambridge, MA.

Nakao et al., "Biliverdin Administration Prevents the Formation of Intimal Hyperlasia Induced by Vascular Injury", Circulation, Jul. 18, 2005, vol. 112, p. 587-591, American Heart Association, Dallas, TX.

Nagira et al., "Ischemia/Reperfusion Injury in the Monolayers of Human Intestinal Epithelial Cell Line Caco-2 and Its Recovery by Antioxidants", Drug Metabolism and Pharmacokinetics, Jul. 21, 2006, vol. 21, No. 3, p. 230-237, Tokyo, Japan.

Schneegurt, Mark; "δ-Aminolevulinic acid biosynthesis in Ustilago maydis", Journal of Basic Microbiology, Apr. 2005, vol. 45, Issue 2, p. 155-159, Wiley, Hoboken, NJ.

Sedlak & Snyder, "Bilirubin Benefits: Cellular Protection by Billiverdin Reductase Antioxidant Cycle", Pediatrics, Jun. 1, 2004, vol. 113, p. 1776-1782, American Academy of Pediatrics, Elk Grove Village, IL.

Sedlak et al., "Bilirubin and Glutathione have Complementary Antioxidant and Cytoprotective Roles", PNAS, Mar. 31, 2009, vol. 106, No. 13, p. 5171-5176, The National Academy of Sciences of the USA, Washington, DC.

Wang et al., "Bilirubin Can Induce Tolerance to Islet Allografts", Endocrinology, Oct. 27, 2005, vol. 147, No. 2, p. 762-768, The Endocrine Society, Chevy Chase, MD.

Yamashita et al.,"Biliverdin, a Natural Product of Heme Catabolism, Induces Tolerance to Cardiac Allografts", The FASEB Journal, Feb. 20, 2004, vol. 18, p. 765-767, FASEB, Bethesda, MD.

Boffelli et al., "Comparative Genomics at the Vertebrate Extremes", Nature Reviews: Genetics, Jun. 2004, vol. 5, p. 456-465, Nature Publishing Group, London, UK.

Krogh et al.,"Hidden Markov Models in Computational Biology: Application to Protein Modeling UCSC-CRL-93-32", Journal of Molecular Biology, Aug. 17, 1993, vol. 235, p. 1501-1531, Elsevier, Cambridge, MA.

Sharp & Li, "The Codon Adaptation Index—A Measure of Directional Synonymous Codon Usage Bias, and its Potential Applications", Nucleic Acids Research. Jan. 1987, vol. 15, No. 3. p. 1281-1295, IRL Press Limited, Oxford, UK.

Ikemura, "Correlation between the abundance of *Escherichia coli* transfer RNAs and the occurrence of the respective codons in its protein genes: A proposal for a synonymous codon choice that is optimal for the *E. coli* translational system", Journal of Molecular Biology, Sep. 25, 1981, vol. 151, Issue 3, p. 389-409, Acedemic Press Inc. Ltd., London, UK.

Link et al., "Methods for Generating Precise Deletions and Insertions in the Genome of Wild-Type *Escherichia coli*: Application to Open Reading Frame Characterization", Journal of Bacteriology, Oct. 1997, vol. 179, No. 20, p. 6228-6237, American Society for Microbiology, Washington, DC.

Khatib, Water to Value-Produced Water Management for Sustainable Field Development of Mature and Green Fields, Journal of Petroleum Technology, Jan. 2003, p. 26-28.

Silveira, Optimization of Phycocyanin Extraction from Spirulina Ethanol Using Factorial Design, 98 (8) Bioresource Technology 1629-1634, Elsevier, Cambridge. MA (2007).

Beuhler, Cleavage of Phycocyanobilin from C-phycocyanin Separation and Mass Apectral Indetification of the Products, Journal of Biological Chemistry, Apr. 25, 1976, p. 2405-2411, vol. 251, No. 8, American Society for Biochemistry and Molecular Biology, Rockville, MD.

Ito et al., Improvement of canine islet yield by donor pancreas infusion with a p38MAPK inhibitor, 86(2) Transplantation 321-329 (2008).

Matsumoto et al., Improvement of pancreatic islet cell isolation for transplantation, 20(4) Proc. (Bayl. Univ. Med. Cent.) 357-362 (2007).

Ito et al., Mesobiliverdin-IXalpha enhances rat pancreatic islet yield and function, 4:50 Frontiers in Pharmacology (Apr. 2013).

Ollinger et al., Bilirubin inhibits tumor cell growth via activation of ERK, Cell Cycle 6:3078-3085 (2007).

Ikeda et al., Biliverdin protects against the deterioration of glucose tolerance in db/db mice, Diabetologia 54:2183-2191 (2011).

Cheng et al., Angiotensin II and vascular inflamation, 11(6) Med Sci Monit 194-205 (2005).

Ollinger et al., Bilirubin and biliverdin treatment of atherosclerotic diseases, 6(1) Cell Cycle 39-43 (2007).

Notification of Transmittal of the International Search Report and the Written Opinion of the Internationl Searching Authority, or the Declaration for PCT/US2013/059998, filed Sep. 16, 2013. Date of Written Opinion mailing is (Jan. 16, 2014).

Kapturczak, et al., Transduction of Human and Mouse Pancreatic Islet Cells Using a Bicistronic Recombinant Adeno-associated Viral Vector, Molecular Therapy, 5 (2) (Feb. 2002).

Wray, et al., Clinical Significance of Bacterial Cultures From 28 Autologous Islet Cell Transplant Solutions, Pancreatology, 5, pp. 562-569 (2005).

U.S. Appl. No. 13/854,791, filed Apr. 1, 2013.
U.S. Appl. No. 13/915,612, filed Jun. 11, 2013.

* cited by examiner

THERAPEUTIC MESO-BILIVERDIN IXα COMPOSITIONS AND ASSOCIATED METHODS

CROSS-REFERENCES TO RELATED APPLICATIONS

This application claims priority to U.S. Provisional Application No. 61/701,465, filed Sep. 14, 2012, the entirety of which is incorporated herein by reference. This application relates to U.S. Pat. No. 8,455,222, issued Jun. 4, 2013; U.S. patent application Ser. No. 13/854,791, filed on Apr. 1, 2013, and to U.S. patent application Ser. No. 13/650,842, filed Oct. 12, 2012, the entireties of which are incorporated herein by reference.

TECHNICAL FIELD

This application relates to compounds, compositions, and methods of their production and use. More specifically, it relates to meso-biliverdin IXα ("MBV"), methods for MBV production, and its use in therapeutic applications.

BACKGROUND

Biliverdin ("BV") IXα (shown below) is the most common form of several BV isomers found in nature.

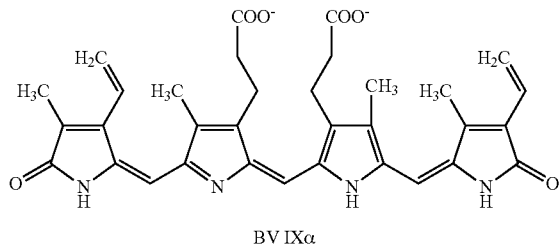

BV IXα

BV IXα is produced in animals, plants and microbes. In biological processes, BV IXα is known to undergo conversion to bilirubin IXα that in turn associates with cell membranes where it quenches the propagation of reactive oxygen species.

BV IXα is being investigated by numerous research groups as a possible therapeutic for various clinical applications. For example, U.S. Pat. No. 8,097,585 and U.S. Patent Application Publication No. 2012/0142751 disclose various therapeutic applications for BV IXα. Various methods of producing BV IXα are also being investigated, as outlined in, for example, U.S. Pat. No. 8,455,222 (by the same primary investigators as in the instant application) and in U.S. Pat. No. 7,504,243 and U.S. Patent Application Publication No. 2009/0203762.

Despite the potential benefits of BV IXα as a therapeutic, additional and alternative therapeutics are desirable.

BRIEF SUMMARY

The present disclosure in aspects and embodiments addresses the above described, and other, needs and problems by providing MBV (shown below) compositions, methods of using MBV, methods of administering MBV and MBV-associated treatment methods.

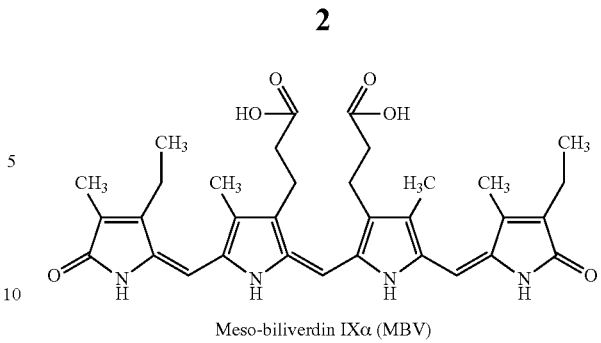

Meso-biliverdin IXα (MBV)

In particular, this application provides pharmaceutical compositions including MBV; methods of treating inflammation in a patient, which include administering a pharmaceutical composition comprising MBV to the patient in an amount effective to reduce inflammation; and methods of transplanting, where the methods include treating an organ to be transplanted with a pharmaceutical composition comprising MBV.

DETAILED DESCRIPTION

Figure 1:
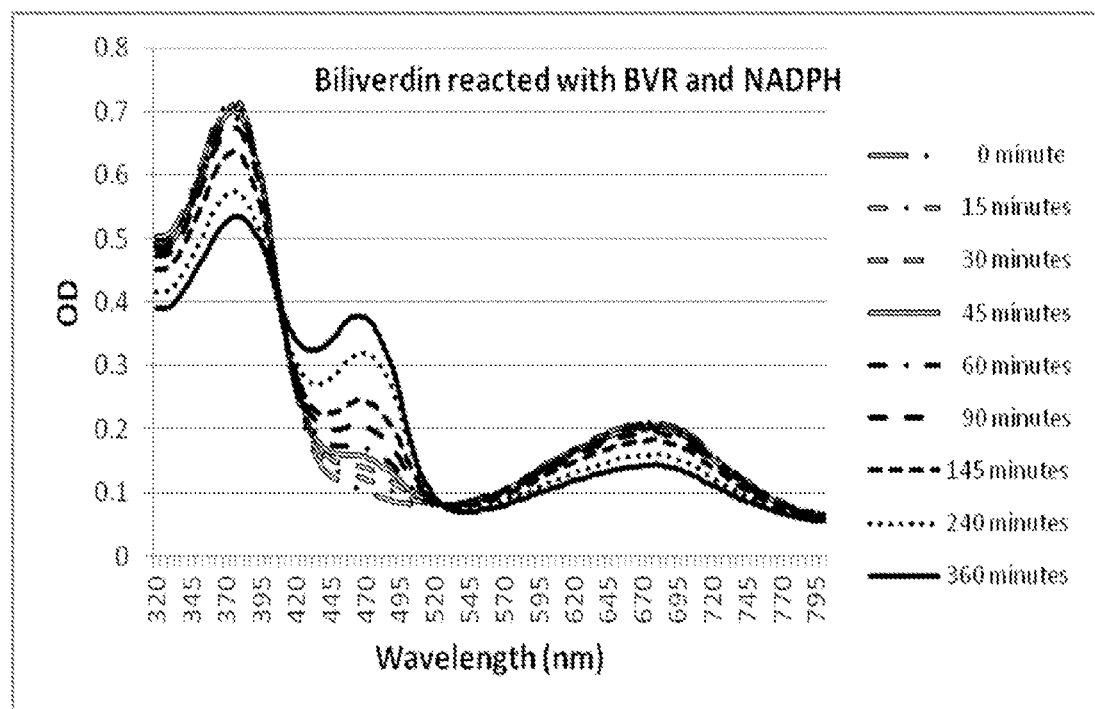
FIG. 1 illustrates the reaction of recombinant human liver BVR enzyme activities with BV IXα.

The present disclosure covers methods, compositions, reagents, and kits relating to MBV and associated MBV therapeutics.

In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

The term "pharmaceutical composition", as used herein, describes a gaseous, liquid, or solid composition, containing an active ingredient, such as MBV, that can be administered to a patient or an organ. Multiple pharmaceutical compositions may be administered in sequence or combination. The form, combination, and sequence of pharmaceutical compositions may vary depending on the disease to be treated and the condition of the patient or organ.

The term "disease", as used herein refers to an abnormal condition affecting the body of an organism or patient. A disease may be caused by external factors or internal dysfunctions and may include any condition that causes pain, dysfunction, distress, or death. Disease includes, but is not limited to, injuries, wounds, disabilities, disorders, syndromes, infections, symptoms, abnormal behaviors, and variations in structure or function of a patient or organism.

The term "organ(s)" as used herein describes any anatomical part or member having a specific function in an organism. Further included within the meaning of this term are substantial portions of organs, such as cohesive tissues obtained from an organ and portions of an organ as small as one cell of the organ. Exemplary organs amenable to the transplantation methods described herein include, but are not limited to kidney, liver, heart, large or small intestine, pancreas, islets, lungs, bones, skin, and blood vessels.

The term "patient", as used herein includes an animal, human or non-human, that is treated according to the methods or with a pharmaceutical composition as described herein.

The terms "effective amount" and "effective to treat," as used herein, refer to an amount or concentration of a pharmaceutical composition over a period of time that when administered to a patient results in an intended benefit or physiological outcome.

The terms "treat" or "treatment," as used herein describe delaying the onset of, inhibiting, or alleviating the effects of a disease.

I. MBV PRODUCTION

MBV for use as a pharmaceutical composition may be produced by any suitable method, including, chemical production or purification from biological sources. MBV, a minor biopigment found naturally in various organisms, is structural isomer of BV, bilirubin, phycoerythrobilin, and phycocyanobilin. U.S. Provisional Application No. 61/546,442, entitled "Meso-Biliverdin, Compositions, Methods, and Applications" describes at least one suitable production method where MBV is produced microbially. This process includes, inter alia, cyanobacterial or algal production, phycocyanobilin extraction, and conversion of phycocyanobilin to MBV.

A. Cyanobacterial and Algal Production

Any phycocyanin-containing cyanobacterial species (also known as a "blue green alga") or rhodophyte or cryptophyte species (also known as a red or cryptomonad alga, respectively) may be used to extract phycocyanin, a bile pigment-protein complex that efficiently harvests light for photosynthetic metabolism. Phycocyanin comprises phycocyanobilin (show below) as the bile pigment chromophore, which is covalently bound (via thiol linkages) to the protein component.

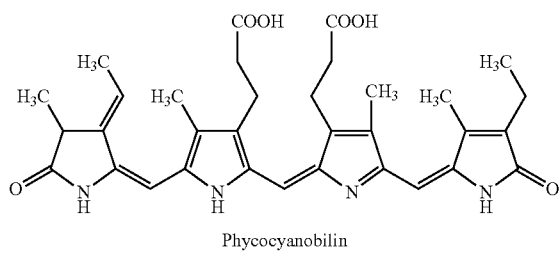

Phycocyanobilin

Some cyanobacteria and rhodophytes will produce phycocyanin in concentrations up to and including ~50% of the total cell soluble protein. Such production may occur when the cyanobacterium, rhodophyte or cryptophyte needs to gather as much light as possible, for example, under low light conditions. As such, cyanobacteria, rhodophytes, and cytophytes with a propensity to produce higher concentrations of phycocyanin are ideally suited for the instant methods. However, any phycocyanin-containing cyanobacterium, rhodophyte, or cryptophyte or one or more species may be used. For example, the cyanobacterium *Arthrospira platensis* (also referred to as Spirulina) may be used.

Any suitable growth medium may also be employed to grow phycocyanin-producing cyanobacteria, rhodophytes and cryptophytes. For example, conventional growth media may also be used. However, polluted and/or waste waters may also be used. Exemplary polluted and/or waste waters include: produced, sanitary, commercial, industrial, agricultural, and/or surface runoff waste water. Produced water is contaminated waste water generated from oil and natural gas recovery operations. An estimated 77 billion gallons of produced water was produced world-wide in 1999 (3 bbl per bbl of crude oil) (Katib and Verbeek, 2003). Produced water is environmentally unsuitable for discharge into surface waters. By using polluted water sources, the water is at least partially cleaned and the bioremediation of the waste water is encouraged.

In some embodiments, the waste water is shaken or otherwise treated to eliminate volatile gases. Depending on the nutrient in the water, the water may be supplemented with sodium nitrate in amounts of from about 15 to about 3000 mg per L, such as about 1500 mg per L, and/or dibasic potassium phosphate in amounts of from about 2 to about 500 mg per L, such as about 200 mg per L.

Growth conditions may include shaking, stirring, and agitating. The culture is exposed to either natural and/or artificial light for periods of two days to two or more weeks depending on nutrient concentrations and culture temperatures. Culture temperatures may be from about 15° C. to about 40° C., such as from about 25° C. to 33° C., or about 26° C.

In some applications, rotating algal bioreactors in large quantities of water may be employed to create biofilms as described in U.S. Patent Application Publication No. 2011/0217764.

B. Extraction of Phycocyanobilin

Any suitable extraction method for extracting phycocyanobilin from the cyanobacteria may be used. Although the culture conditions described above may be employed, any source of cyanobacteria may be used in the extraction process. If the cells are in a culture medium, they must first be harvested or further concentrated. The cells may be lysed and dried or lysed and kept in a slurry, paste, or partially dried condition. In some embodiments, pre-dried cyanobacteria, rhodophytes or cryptophytes, such as pre-dried Spirulina, may be used as a phycocyanobilin source rather than cultured organisms.

In some embodiments, the extraction process may be separated into the following steps: (1) phycocyanin extraction, (2) cleavage of phycocyanobilin from phycocyanin, and (3) phycocyanobilin purification.

Any suitable bacterial cell breakage and fractionation method may be used for extraction and recovery of phycocyanin. For example, a slurry containing water and cyanobacterial cells may be prepared by shaking, centrifugation to sediment cells, cell breakage (mechanical or chemical), centrifugation to sediment unbroken cells and debris, and recovery of non-sedimenting cell extract, followed by the addition of ammonium sulfate (($NH_4)_2SO_4$) to precipitate phycocyanin. After incubation and additional centrifugation, sedimented dark-blue phycocyanin may be collected and washed with a washing solvent, for example, methanol or ethanol. See, e.g., Silveira et al., Optimization of phycocyanin extraction from Spirulina platensis using factorial design, 98(8) Bioresour Technol. 1629-34 (2007).

Cleavage of phycocyanobilin from phycocyanin may be undertaken by any suitable method. For example, phycocyanin may be boiled in a solvent, such as methanol or ethanol, under reflux conditions to cleave the bonds between the pigment and protein. See, Beuhler et al., Cleavage of phycocyanobilin from C-phycocyanin. Separation and mass spectral identification of the products, 251(8) J. Biol. Chem. 2405-2411 (1976).

The phycocyanobilin may be further concentrated and purified by centrifugation, or other suitable purification method, followed by extraction of the phycocyanobilin by a suitable method, such as with chloroform. After this extraction, the chloroform solution may be added to an organic solvent, such as hexane, followed by centrifugation to yield pure phycocyanobilin powder.

C. Conversion of Phycocyanobilin to MBV

To yield the desired MBV, an isomerization of phycocyanobilin is carried out. In the past, isomerization and/or oxidation was carried out with potassium hydroxide (KOH), methanol (MeOH), and chloroform. See, e.g., id. As an alternative to using the caustic and harsh reactants, particularly KOH, an alternative method of isomerization is described below.

To isomerize phycocyanobilin to MBV, phycocyanobilin is dissolved in a solvent along with an amphoteric compound. Suitable amphoteric compounds include, for example, sodium bicarbonate ($NaHCO_3$), potassium carbonate ($K_2CO_3$), sodium carbonate, and combinations thereof. Suitable solvents include, for example, ethanol (EtOH), such as reagent grade ethanol (95%). Similarly, tert-butyl alcohol may be used as a solvent.

The ratios of the reagents may be varied. In some embodiments, 1 to 5 folds, such as 3, 4, or 5 folds, in weight of $NaHCO_3$ and $K_2CO_3$ compared to phycocyanobilin may be used. A sufficient amount of solvent may be used to dissolve the reactants. For example, about 3 mL ethanol may be used with about 5 mg phycocyanobilin.

The reaction is permitted to run for about 12-48 hours, such as from about 24-48 hours, or about 24 hours at about 80° C. The reaction mixture may be filtered through Celite and the residue was washed and filtered with more ethanol. The solvent may removed to provide the MBV and may be further purified if desired by HPLC.

This isomerization reaction has numerous advantages over prior methods, such as the method mentioned above. Advantages include, for example, 1) avoiding the use of KOH, which is caustic and can be difficult to dispose of after product purification; and 2) avoiding the use of methanol and chloroform, which are toxic and can also be difficult to dispose of after purification.

In some embodiments, the entire process of (1) microbial production, (2) phycocyanobilin extraction, and (3) conversion of phycocyanobilin to MBV may be carried out with natural compounds, such as ethanol for a reaction solvent and washing solvent.

II. MBV AS A THERAPEUTIC

MBV produced by the above method, or any other suitable method, may be used as a therapeutic to treat disease in patients.

A. Effective Amounts

In treating patients, effective amounts of MBV include, for example, from about 1 to 1000 micromoles/kg/day, such as at least 10, 20, 30, 40, 50, 60, 70, 80, 90, 100, 200, 300, 400, 500, 600, 700, 800, or 900 micromoles/kg/day. In addition, effective amounts include amounts that exceed 1000 micromoles/kg/day. Amounts outside the above described ranges may also be used depending upon the disease to be treated and the patient's response to the treatment.

In some embodiments, MBV may be combined with BV IXα or heme oxygenase-1, or any other products of heme degradation heme oxygenase-1. MBV may also be combined with Effective Amounts of one or more other pharmaceutically effective compositions, such as antibiotics, antifungals, antivirals, anti-inflammatories, analgesics, antipyretics, antiseptics, antihistamines, anti-allergics, anesthetics, vaccines, or combinations thereof.

In determining the effective amount of MBV compounds, conventional techniques may be employed. For example, the toxicity and therapeutic efficacy of MBV compounds may be determined by standard pharmaceutical procedures in cell cultures or experimental animals. For instance, the LD50 (the dose lethal to 50% of the population) and the ED50 (the dose therapeutically effective in 50% of the population) may be determined according to these standard pharmaceutical procedures. The therapeutic index may thus be expressed as the ratio LD50/ED50.

The dosage, and/or a range of dosages, for use in humans may be determined from the above described data obtained from the cell culture assays and animal studies. The dosage of such compounds may lie within a range of circulating concentrations that include the ED50 with little or no toxicity. The dosage may vary within this range depending upon the dosage form employed and the route of administration utilized. For any compound used in the method described herein, a therapeutically effective dose may be estimated initially from cell culture assays and then further formulated in animal models to achieve a circulating plasma concentration range that includes the IC50 (i.e., the concentration of the test compound which achieves a half-maximal inhibition of symptoms) as determined in cell culture. Such information may be used to more accurately determine useful doses in humans. Levels in plasma can be measured, for example, by high performance liquid chromatography.

B. Methods of Delivery

MBV compositions may be induced, expressed, or delivered to a patient in need of treatment. Conventional routes of delivery include, for example, oral, topical, parenteral, intravenous, subcutaneous, intramedullary, intranasal, rectal, or buccal administering. MBV or MBV compositions may also be administered via gene therapy, gene transfer, or upregulation of MBV production within the patient.

MBV compositions may be delivered alone or in combination with pharmaceutically acceptable carriers, vehicles or diluents, in a single dose, multiple doses, or constant infusion. Suitable pharmaceutical carriers, vehicles, and diluents include inert solid diluents or fillers, sterile aqueous solutions and various organic solvents. Adjuvants may also be added to the MBV compositions.

The pharmaceutical compositions formed by combining the MBV compositions and the pharmaceutically acceptable carriers, vehicles, diluents, and/or adjuvants are then readily administered in a variety of dosage forms such as tablets, powders, lozenges, syrups, injectable solutions, and the like. These pharmaceutical compositions may, if desired, contain additional ingredients such as flavorings, binders, excipients and the like.

In oral delivery, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral delivery, solutions of the MBV compositions in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Topical delivery may also be used for wound treatment, in surgical applications, for treatment of gastrointestinal disorders, or whenever the medication is best applied to the surface of a tissue or organ as determined by the attending physician. For purposes of transdermal administration, dilute sterile, aqueous or partially aqueous solutions (usually in about 0.1% to 5% concentration), otherwise similar to the above parenteral solutions, may be prepared.

For intranasal delivery or delivery by inhalation, the MBV compound may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Increased levels of MBV within a patient or target organ within a patient may be generated via gene therapy or gene transfer. In such treatment techniques, a gene therapy vector, such as a plasmid, virus (lentivirus, adenovirus, adeno-associated virus) that encodes genes for MBV biosynthesis and with the appropriate expression control sequence or that encodes the appropriate expression control sequence may be administered to a patient or an organ of a patient by any of the administration techniques described above that is appropriate for the administration of the vector.

In some therapeutic applications, a combination of multiple inducement, administration, and/or expression techniques may be employed.

Methods of preparing various pharmaceutical compositions with a certain amount of active ingredient are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

C. Diseases for Treatment

The compositions and methods described herein may be used to treat one or more diseases, including, for example, autoimmune diseases, inflammatory diseases, infectious diseases, renal diseases, hepatobiliary diseases, heart diseases, gastrointestinal diseases, respiratory diseases, thyroid diseases, neurodegenerative diseases, venereal diseases, and cellular proliferative and/or differentiative diseases (such as cancer). The compositions and methods may also be used to promote wound healing and surgical transplantation applications.

Exemplary inflammatory diseases that may be treated with the compositions and methods described herein include any and all diseases where the inflammatory pathways within a patient or organ of a patient have been stimulated, are irregular, or are in need of some degree of control to aid in the treatment and/or recovery of a patient. The types of inflammation that may be treated include, but are not limited to, acute, chronic, allergic (including conditions involving mast cells), alternative (degenerative), atrophic, catarrhal (most frequently in the respiratory tract), croupous, fibrinopurulent, fibrinous, immune, hyperplastic or proliferative, subacute, serous and serofibrinous. Localized inflammation at a site of bodily trauma, injury, transplantation, or within an organ or portion thereof, including, for example, the gastrointestinal tract, kidneys, liver, heart, skin, spleen, brain, kidney, pulmonary tract, and lungs may be treated according to the compositions and methods described herein.

Exemplary autoimmune diseases, and/or autoimmune-related diseases, that may be treated with the compositions and methods described herein include, but are not limited to Acute Disseminated Encephalomyelitis (ADEM), Acute necrotizing hemorrhagic leukoencephalitis, Addison's disease, Agammaglobulinemia, Alopecia greata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease Autoimmune urticarial, Axonal & neuronal neuropathies, Balo disease, Behcet's disease, Bullous pemphigoid, Cardiomyopathy, Castleman disease, Celiac disease, Chagas disease, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Diabetes mellitus (including Type 1 diabetes mellitus, Type 2 diabetes, gestational diabetes, prediabetes, latent autoimmune diabetes of adults), Discoid lupus, Dressler's syndrome, Endometriosis, Eosinophilic esophagitis, Eosinophilic fasciitis, Erythema nodosum, Experimental allergic encephalomyelitis, Evans syndrome, Fibrosing alveolitis, Giant cell arteritis (temporal arteritis), Glomerulonephritis, Goodpasture's syndrome, Granulomatosis with Polyangiitis (GPA) see Wegener's, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes (type1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, and Wegener's granulomatosis (now termed Granulomatosis with Polyangiitis (GPA).

Exemplary infectious diseases that may be treated with the compositions and methods described herein include, but are not limited to bacterial, viral, fungal, parasitic, and protozoan infections. In particular, the compositions and methods described herein may be used to treat or prevent inflammation associated with infection.

Exemplary renal diseases that may be treated with the compositions and methods described herein include, but are not limited to, pathologies of glomerular injury such as in situ immune complex deposition and cell-mediated immunity in glomerulonephritis; damage caused by activation of alternative complement pathway, epithelial cell injury; pathologies involving mediators of glomerular injury including cellular and soluble mediators; acute glomerulonephritis, such as acute proliferative glomerulonephritis, e.g., poststreptococcal glomerulonephritis and nonstreptococcal acute glomerulonephritis, rapidly progressive glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis) and chronic glomerulonephritis. Disorders of the kidney also include infections of the genitourinary tract.

Exemplary hepatobiliary diseases that may be treated with the compositions and methods described herein include, but are not limited to, cirrhosis and infectious disorders such as viral hepatitis, including hepatitis A-E viral infection and infection by other hepatitis viruses, clinicopathologic syndromes, acute viral hepatitis, chronic viral hepatitis, and fulminant hepatitis; and drug- and toxin-induced liver disease, such as alcoholic liver disease.

Exemplary cardiovascular diseases that may be treated with the compositions and methods described herein include disorders involving the cardiovascular system and circulatory system, such as the heart, the blood vessels, and/or the blood. These diseases include, but are not limited to, congestive heart failure, peripheral vascular disease, pulmonary vascular thrombotic diseases such as pulmonary embolism, stroke, ischemia-reperfusion (I/R) injury to the heart, atherosclerosis, heart attacks, ischemia, and shock.

Exemplary gastrointestinal diseases that may be treated with the compositions and methods described herein include, but are not limited to, ileus of any portion of the gastrointestinal tract (the large or small intestine), inflammatory bowel disease, specific inflammatory bowel disease, infective specific inflammatory bowel disease, amoebic or bacillary dysentery, schistosomiasis, *campylobacter enterocolitis, yersinia enterocolitis, enterobius vermicularis*, non-infective specific inflammatory bowel disease, radiation enterocolitis, ischaemic colitis, or eosinophilic gastroenteritis, non-specific bowel disease, ulcerative colitis, indeterminate colitis, Crohn's disease, necrotizing enterocolitis (NEC), and pancreatitis.

Exemplary respiratory diseases that may be treated with the compositions and methods described herein include, but are not limited to, asthma, Acute Respiratory Distress Syndrome (ARDS) (such as ARDS caused by peritonitis, pneumonia (bacterial or viral), or trauma), idiopathic pulmonary diseases, interstitial lung diseases, Interstitial Pulmonary Fibrosis (IPF), pulmonary emboli, Chronic Obstructive Pulmonary Disease (COPD), emphysema, bronchitis, cystic fibrosis, lung cancer of any type, lung injury, hyperoxic lung injury, Primary Pulmonary Hypertension (PPH), secondary pulmonary hypertension, and sleep-related disorders (such as sleep apnea).

Exemplary neurological diseases that may be treated with the compositions and methods described herein include, but are not limited to disorders involving the brain, degenerative diseases affecting the cerebral cortex, including Alzheimer's disease, degenerative diseases of basal ganglia and brain stem, Parkinsonism, and idiopathic Parkinson's disease (paralysis agitans).

Exemplary venereal and reproductive diseases that may be treated with the compositions and methods described herein include, but are not limited to chancroid, chlamydia, granuloma inguinale, gonorrhea, syphilis, candidiasis, viral hepatitus, herpes simplex, HIV, HPV, mulloscum contagiosum, crab louse, scabies, trichomoniasis. In particular, the compositions and methods described herein may be used to treat or prevent certain impotence and/or inflammation associated with sexually transmitted diseases. Further, the compositions and methods may be used to treat or prevent premature uterine contractions, premature deliveries, and menstrual cramps.

Exemplary cellular proliferative and/or differentiative diseases that may be treated with the compositions and methods described herein include, but are not limited to cancers, sarcomas, carcinomas, adenocarcinomas, metastatic disorders or hematopoietic neoplastic disorders, and leukemias such as: cancers of the stomach, colon, rectal, liver, pancreatic, lung, breast, cervix uteri, corpus uteri, ovary, prostate, testis, bladder, renal, brain/central nervous system, head and neck, throat, mouth/pharynx, esophagus, larynx, kidney, and skin; Hodgkins disease; non-Hodgkins leukemia; skin melanoma; small cell lung cancer; choriocarcinoma; melanoma; and lymphoma.

In addition to the above listed exemplary diseases, the compositions and methods described herein may also be used to treat or prevent pain, such as the pain response resulting from various forms of tissue injury, such as inflammation, infection, and ischemia, usually referred to as hyperalgesia; pain associated with musculoskeletal disorders, such as joint pain, tooth pain, and headaches; pain associated with surgery; pain related to irritable bowel syndrome; or chest pain. Also included in this category are seizure disorders, such as epilepsy.

D. Wound Healing

The compositions and methods are additionally suited to the promotion of wound healing. In wound healing, the compositions may be administered in any of the above described methods of administration. In some embodiments, the compositions, in pharmaceutical form, are injected and/or topically administered. Topical administration may include ointments, creams, salves, or solutions including the compositions. Exemplary wounds include, but are not limited to, open and closed wounds, such as lacerations, incisions, abrasions, puncture wounds, penetration wounds, burns scraps, rashes, blisters, contusions, hematomas, and crush injuries.

E. Surgery

Similarly, the compositions and methods are additionally suited to surgical applications. In wound healing, the compositions may be administered in any of the above described methods of administration. In some embodiments, the compositions, in pharmaceutical form, are injected and/or topically administered. Exemplary surgical applications include, but are not limited to, bariatric, cardiac, cardiothoracic, colon and rectal, neurosurgery, obstetrics, oncologic, ophthalmology, oral, orthopedic, otolaryngology, pediatric, cosmetic and reconstructive, podiatry, thoracic, trauma, and vascular surgery.

F. Transplantation

The compositions and methods described herein may also be used in transplantation applications. In such applications, the compositions exhibit cytoprotective properties that may result in increased cell harvests yields, more successful organ harvests, increased viability in transplanted cells and organs, and subsequent wound healing after the transplantation procedure has occurred.

In embodiments, methods may be used to treat donors, recipients, organs, and/or transplantation/donor sites during any step of the transplantation process, which may includes organ harvesting, storage, and transplant.

The transplantation processes described herein include all categories of transplants known in the art, such as, for example, autotransplantation (removal and transfer of cells or tissue from one location on a patient to the same or another location on the same patient), allotransplantation (transplantation between members of the same species), and xenotransplantation (transplantations between members of different species).

In embodiments, an organ to be donated may be treated with a pharmaceutical composition prior to, during, and/or after it is harvested from the donor. When treated prior to harvesting, the organ may be treated in situ by administering a pharmaceutical composition to the patient or directly to the organ. When treated after harvesting, the organ may be treated ex vivo by exposing the organ to an atmosphere comprising a gaseous pharmaceutical composition, to a liquid pharmaceutical composition (a liquid perfusate, storage solution, or wash solution containing the pharmaceutical composition) or to both. Alternatively or in addition, the organ may be treated after transplantation into the recipient. A pharmaceutical composition may also be administered to the recipient prior to, during, and/or after the surgery.

When exposing an organ to a gaseous pharmaceutical composition, such as one comprising carbon monoxide, the exposure may be performed in any chamber or area suitable for creating an atmosphere that includes appropriate levels of carbon monoxide gas. Exemplary chambers include incubators and chambers built for the purpose of accommodating an organ in a preservation solution. An appropriate chamber can be a chamber wherein only the gases fed into the chamber are present in the internal atmosphere, such that the concentration of carbon monoxide may be established and maintained at a given concentration and purity, e.g., where the chamber is airtight. For example, a $CO_2$ incubator may be used to expose an organ to a carbon monoxide composition, wherein carbon monoxide gas is supplied in a continuous flow from a vessel that contains the gas.

When exposing an organ to an aqueous pharmaceutical composition, the exposure may be performed in any chamber or space having sufficient volume for submerging the organ, completely or partially, in an aqueous pharmaceutical composition. As yet another example, the organ may be exposed by placing the organ in any suitable container, and causing a liquid pharmaceutical composition to "wash over" the organ, such that the organ is exposed to a continuous flow of the composition.

In embodiments where the pharmaceutical compositions comprises carbon monoxide, the organ may be placed or submerged in a medium or solution that does not include carbon monoxide, and placed in a chamber such that the medium or solution can be made into a carbon monoxide composition via exposure to a carbon monoxide-containing atmosphere as described herein. In addition, the organ may be submerged in a liquid that does not include carbon monoxide, and carbon monoxide may be "bubbled" into the liquid.

When perfusing an organ with an aqueous pharmaceutical composition, the organ may be perfused ex vivo or in situ. Methods for perfusing organs ex vivo and in situ are well known in the art. The aqueous pharmaceutical solution may be allowed to remain in the vasculature for a given length of time. Optionally, in in situ or ex vivo perfusions, the organ may be perfused with a wash solution, e.g., UW solution without a pharmaceutical composition, prior to perfusion with the aqueous pharmaceutical composition to remove the donor's blood from the organ. Such a process may be advantageous, for example, when using pharmaceutical compositions comprising carbon monoxide, to avoid competition for carbon monoxide by the donor's hemoglobin. As another option, the wash solution itself may be a pharmaceutical composition, such as a pharmaceutical composition comprising carbon monoxide The skilled practitioner will recognize that methods for transplanting and/or harvesting organs for transplantation can vary depending upon many circumstances, such as the age of the donor/recipient or the nature of the organ being transplanted. Any or all of the above methods for exposing an organ to a pharmaceutical composition, e.g., gassing, washing, submerging, or perfusing, can be used in a given procedure.

V. EXAMPLES

The following examples are illustrative only and are not intended to limit the disclosure in any way.

Example 1

Phycocyanin-Containing Cyanobacteria or Alga Production

*Arthrospira platensis* was grown on produced water that has been previously shaken for several days to eliminate volatile gases and supplemented with sodium nitrate and potassium phosphate. Growth occurred with shaking and fluorescent light over several days to two weeks at 26° C. The cells were then harvested and dried.

In addition, cyanobacterial biofilms were propagated in produced water and municipal-waste water utilizing a Rotating Algal Biofilm Reactor (RABR), biomass was directly harvested from the RABR and processed to extract phycocyanin that in turn was used to produce MBV. Undiluted Wyoming Produced Water (amended with 3.0 g/L $NaNO_3$+ 0.5 g/L $K_2HPO_4$), 18°-22° C., light=220 mmol/$m^2$-s was inoculated with cyanobacteria (Logan Lagoon Cyanobacteria isolate 2 (LLC2) to propagate RABR biofilms. RABR units were used directly in Logan City municipal waste treatment lagoons to propagate cyanobacterial biofilms. Biofilms were harvested, lyophilized, and pulverized to a powder. The powdered biomass was extracted with either water or with 50 mM sodium phosphate buffer @ pH 7.0 for 2 hours and phycocyanin recovered. Phycocanobilin was extracted from phycocyanin as described in Example 2 and chemically converted to MBV as described in Example 3.

Example 2

Phycocyanobilin Extraction

Phycocyanin Extraction.

The extraction was carried out by adding 160 g Spirulina powder to 2 L (2000 mL) of purified water (0.08 g/mL) and shaking in a rotary shaker overnight (16 hours) at 200 rpm and 37° C. The sample was centrifuged for 90 minutes at 9500 rpm at 4° C. $(NH_4)_2SO_4$ (MW. 132.14) (530 g) was added to the supernatant fraction to give a 50% saturated $(NH_4)_2SO_4$ solution. The solution was incubated in ice water (0° C.) for 30 minutes. After centrifugation at 9500 rpm for 30 minutes, the precipitated dark-blue Phycocyanin was washed by suspension in 700 mL methanol followed by centrifugation and discarding the supernatant fluid. The washing procedure was repeated 4 times each with 300 mL methanol, and purified Phycocyanin was recovered as pelleted material.

Cleavage of Phycocyanobilin from Phycocyanin.

Phycocyanobilin was cleaved by boiling the Phycocyanin in 600 mL methanol under reflux with stirring for 16 hours.

Phycocyanobilin Purification.

After centrifugation at 6000 rpm 5 minutes, the volume of supernatant was reduced to around 40 mL by a rotary evaporator. Concentrated phycocyanobilin solution and 25 mL chloroform was added to 200 mL purified water acidified with 300 µL 0.5N HCl. The mixture was vortexed and allowed to partition and extract Phycocyanobilin into the chloroform phase. The chloroform extraction procedure was repeated three times with 10 mL chloroform. The chloroform fractions were pooled and the combined chloroform solution volume was reduced to around 10 mL by evaporation with nitrogen gas. The chloroform solution was added to 60 mL hexane. Phycocyanobilin was collected by centrifugation for 3 minutes at 5000 rpm. After air drying, purified Phycocyanobilin was obtained. Typically, 100 to 150 mg of Phycocyanobilin was recovered from 160 g of Spirulina.

Example 3

Phycocyanobilin Conversion to MBV

In 3 mL of reagent grade ethanol, 5 mg of purified Phycocyanobilin was mixed with 20 mg of $NaHCO_3$ and 20 mg of $K_2CO_3$ and incubated for 1 day at room temperature for conversion to MBV IXα. Approximately, 5 mg of MBV (shown below) was produced from 5 mg starting material.

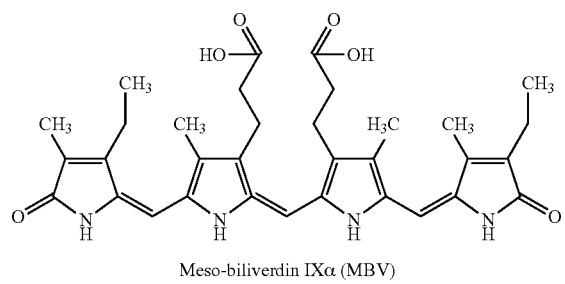

Meso-biliverdin IXα (MBV)

Example 4

MBV Interaction with Biliverdin Reductase

BVR Enzyme Assay.

The Sigma-Aldrich (St. Louis, Mo.) Biliverdin Reduction Kit (catalog #CS1100) and method was used to determine biliverdin reductase ("BVR") activities with MBV, BV IXα, or phycocyanobilin as substrates. The kit-supplied enzyme was human liver BVR expressed in a recombinant *Escherichia coli* strain. Before use, MBV, BV IXα, or phycocyanobilin, each at 100 µg $mL^{-1}$ in methanol, were diluted 10-fold in the kit-supplied assay buffer, mixed with enzyme and NADPH, and conversion to mesobilirubin IXα, bilirubin IXα, or phycocyanobilirubin was measured spectrophotometrically between 300 and 800 nm for up to 360 minutes.

Figure 2:
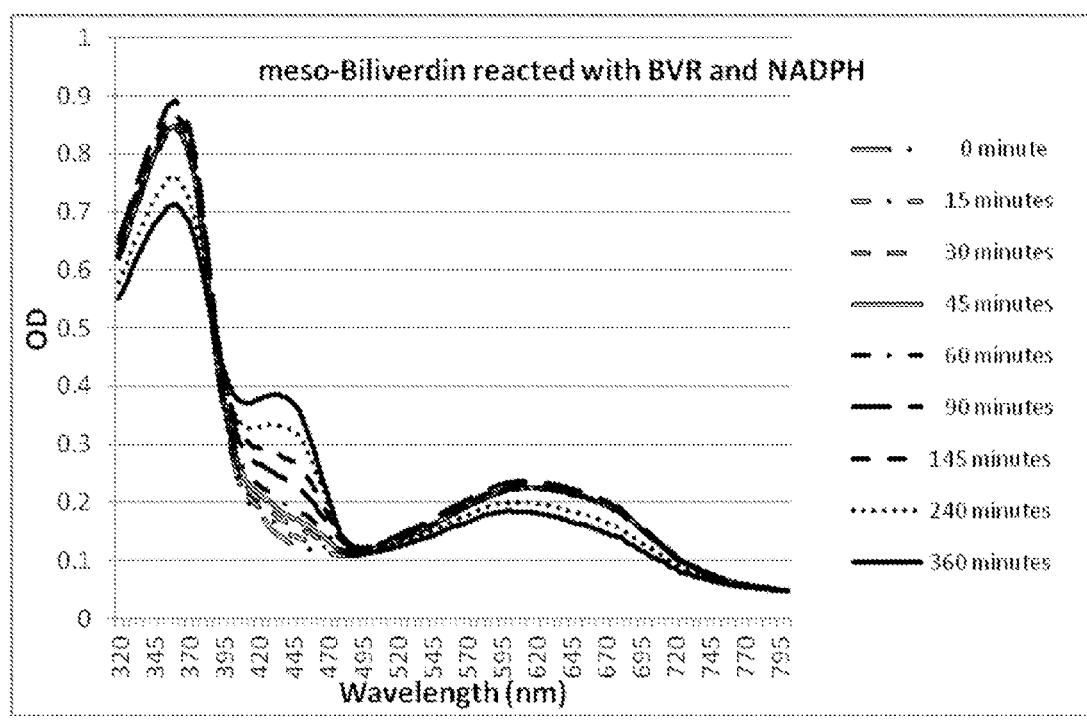
FIG. 2 illustrates the reaction of recombinant human liver BVR enzyme activities with MBV IXα.
Figure 3:
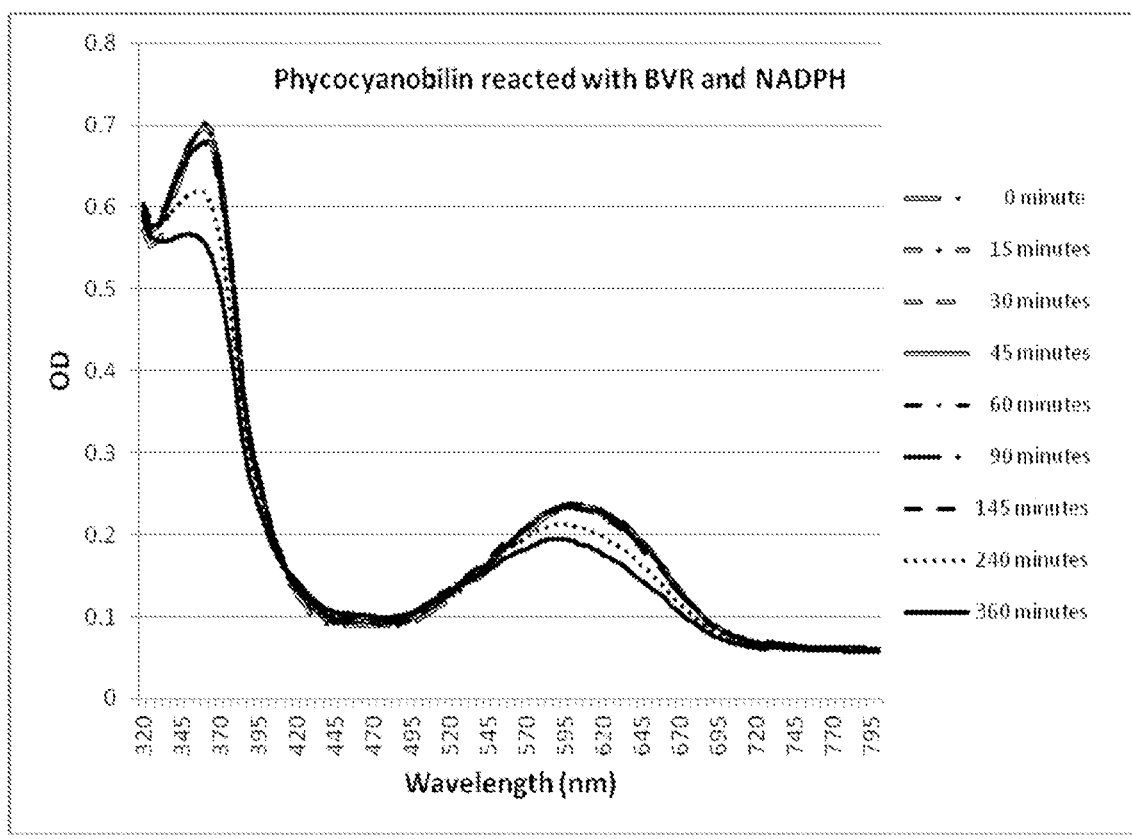
FIG. 3 illustrates the reaction of recombinant human liver BVR enzyme activities with phycocyanobilin.

MBV Conversion to Mesobilirubin IXα (FIGS. 1-3).

MBV served as substrate and was catalytically converted to mesobilirubin IXα by recombinant human liver BVR with kinetics that resembled those for BV IXα conversion to bilirubin IXα.

These results indicate that MBV (like BV IXα) interacts with human BVR to initiate cell signaling events that lead to promotion of anti-inflammatory processes and suppression of pro-inflammatory processes. In contrast the bile pigment phycocyanobilin is a poor and relatively inactive catalytic substrate for this enzyme.

FIGS. 1-3 illustrate the above results: Recombinant human liver BVR enzyme activities using BV IXα (FIG. 1), MBV (FIG. 2) and phycocyanobilin (FIG. 3) as substrates. Spectral peaks between 420 and 470 nm represent the reduced enzymatic products bilirubin IXα, mesobilirubin IXα and phycocyanobilirubin, respectively of BV IXα, MBV and phycocyanobilin.

Example 5

Islet Cell Yields after Treatment of Donor Pancreata

MBV and BV IXα Treatment of Pancreata and Islet Cell Isolation.

MBV and BV IXα (obtained from Frontier Scientific, Inc., Logan Utah) (both at 1, 10, or 100 μM) were administered to IVC-dissected animals through the pancreatic duct at 37° C. Control animals received no treatment. Pancreata were removed from donor rats (Lewis, BW>300 g), incubated with University of Wisconsin solution and preserved using the two-layer method. See Ito et al., *Improvement of canine islet yield by donor pancreas infusion with a p38MAPK inhibitor*, Transplantation 86(2): 321-329 (2008). After 20 to 22 hours, islet cells were isolated using the 2-step digestion method after distention with collagenase and then purified by discontinuous Ficoll gradient centrifugation in a COBE 2991 cell processor. See Matsumoto et al., *Improvement of pancreatic islet cell isolation for transplantation*, Proc. (Bayl. Univ. Med. Cent.) 20(4): 357-362 (2007). Islet cells were counted microscopically and the numbers converted to IEQ (number of islets equivalent to 150 um in diameter.

Effect on Islet Cell Yield.

MBV-treated pancreata yielded significantly more islets than did untreated control pancreata (IEQ/g: 1599±475 (1 μM) and 1318±804(10 μM) vs. 856±229 (control); P<0.05). Commercially obtained BV IXα-treated pancreata also yielded more islets than the control (IEQ/g: 1328±358 (1 μM) and 1616±451 (10 μM) vs. 1193±223 (control); P<0.05). For both MBV and BV IXα, 100 μM concentration did not increase islet yields beyond those with 10 μM concentration. Therefore, 1 μM and 10 μM MBV increased islet yields 1.87-fold and 1.54-fold, respectively, and 1 μM and 10 μM commercial BV IXα, 1.04-fold and 1.24-fold, respectively, over non-treated controls. See Ito et al., Mesobiliverdin-IXα Enhances Rat Pancreatic Islet Yield and Function, 4:50 Frontiers in Pharmacology (2013), the entirety of which is herein incorporated by reference.

Example 6

Treatment of Donor Pancreata Followed by Islet Cell Transplantation

Transplantation of Islet Cells from Donor Pancreata Treated with MBV.

Pancreata removed from donor rats (Lewis, BW>300 g) were infused with University of Wisconsin solution containing MBV or BV IXα at 1, 10, or 100 μM through the pancreatic duct and preserved using the 2-layer method in Hank's balanced salt solution containing 5% autologous serum as described in Example 5. After 20 to 22 hours, islets were isolated and 3000 IEQ/kg were autotransplanted by infusion into the portal vein of the corresponding rat.

Transplanted Islet Cell Yield and Function in Recipients.

Islet cell yields (IEQ values) assessed by laser scanning cytometry were higher and transplantation with MBV-treated donor pancreata were similar or more efficacious versus using islets derived from untreated control pancreata. Tumor necrosis factor α expression assessed by real-time reverse transcription polymerase chain reaction were significantly lower in the MBV-treated group than controls. Recipient rats transplanted with MBV-treated islets were more euglycemic than rats receiving untreated islets. Plasma C peptide levels after glucagon challenge were higher in animals receiving MBV-treated islets than those receiving islets from untreated control pancreata.

Thus, infusion of pancreata with MBV through the duct before preservation suppresses cytokine release, prevented islet cell apoptosis, and improved islet yield significantly with no adverse effect on islet function.

Example 7

Effect on Colonic Cancer Cell Proliferation and Tumor Growth

MBV Treatment of HRT-18 Colon Cancer Cells and Tumors.

HRT-18 cells are seeded in 6-well plates in a concentration of $25 \times 10^4$ cells per well. After 24 hours, incubation, cells are treated with MBV IXα (1, 10, and 100 μM) or phosphate buffered saline (PBS) as a control. Cells are washed, detached with trypsin and resolved in 1 mL of growth media. 100 μL of cell lysate are then analyzed for cell number, viability and cell size. In a xenograft colonic tumor model (see Ollinger et al., *Bilirubin Inhibits Tumor Cell Growth via Activation of ERK*, Cell Cycle 6:3078-3085 (2007)), $2.5 \times 10^6$ HRT 18 colon cancer cells are injected subcutaneously into the lower flank of BALB/c nude mice. At 14 days, MBV treatment is begun by injection of 1, 10 and 100 mg/kg body weight or PBS (controls) twice daily intraperitoneally and tumor diameters are measured daily using a caliper.

Colonic Cancer Cell Growth and Tumor Formation.

MBV reduces HRT-18 colonic cell proliferation in vitro and xenograft tumor formation in vivo at higher rates than untreated controls. Effects by MBV levels that resemble serum bile pigment levels support the hypothesis that BV/bilirubin are potent suppressors of tumor growth and could explain the observed inverse correlation of cancer incidence and serum levels of this compounds. See Ollinger et al., *Bilirubin Inhibits Tumor Cell Growth via Activation of ERK*, Cell Cycle 6:3078-3085 (2007).

Example 8

Effect on Glucose Tolerance in Type 2 Diabetes

Feeding Diabetic and Obese Subjects and Monitoring Parameters of Type 2 Diabetes.

MBV (2, 20 and 100 mg kg$^{-1}$ daily) is orally administered to 5-week-old db/db and obese mice for 4 weeks. Control mice are given the same feed without added MBV. After 4 weeks, glucose tolerance and insulin tolerance tests are performed. See Ikeda et al., *Biliverdin protects against the deterioration of glucose tolerance in db/db mice*, Diabetologia 54:2183-2191 (2011). Insulin content is evaluated by immunostaining and ELISA. Oxidative stress markers (8-hydroxy-2'-deoxyguanosine and dihydroethidium staining) and expression of NADPH oxidase components Pdx1 and Bax are evaluated in isolated islets.

Protection Against Progressive Glucose Tolerance.

MBV feeding at least partially prevents development of hyperglycemia and glucose intolerance in db/db and obese mice. Insulin levels and Pdx1 expression increases, decreases of apoptosis and Bax expression in islets from db/db mice are observed, and levels of oxidative stress markers and NADPH oxidase activities are lower and normal compared to those of controls Thus, feeding subjects MBV protects against the development of type 2 diabetes via mechanisms associated with suppression of oxidative damage of pancreatic islet cells. See Ikeda et al., *Biliverdin protects against the deterioration of glucose tolerance in db/db mice*, Diabetologia 54:2183-2191 (2011).

Example 9

Suppression of Angiotensin II-Induced Cardiovascular Inflammation

MBV Suppression of Superoxide Anion Production by A7r5 Cells Exposed to Angiotensin II.

Rat thoracic aortic vascular smooth muscle (A7r5) cells cultured in Dulbecco's modified Eagle's medium supplemented with 10% fetal calf serum and 2 mM glutamine are exposed to various concentrations of angiotensin II and MBV for various lengths of time before harvesting. The cells are scraped into balanced salt solution, washed twice by centrifugation, and finally suspended at a density of $2 \times 10^6$ cells per mL in the same solution containing 10 mM glucose and 1 mg per mL bovine serum albumin. Superoxide anion levels (of suspensions with $9 \times 10^5$ cells) are measured with a luminometer and a commercial luminogen-based detection kit (LumiMax, Agilent Technologies. Inc.).

MBV Inhibition of Microsomal NADH/NADPH Oxidase Activity of Angiotensin II-Treated A7r5 Cells.

Angiotensin II and MBV-treated cells suspended in phosphate-buffered saline (with protease inhibitors) are disrupted at ice temperature using a Dounce homogenizer. The cell extracts are fractionated into microsomal membrane and cytosol fractions by standard differential centrifugation procedures. Microsomes, containing plasma and mitochondrial membranes, are recovered as pellets after centrifugation at 29,100 g for 20 min at 4° C. NADH/NADPH oxidase activities of the microsomal fractions are measured with a luminometer and a commercial luminogen-based kit (LumiMax, Agilent Technologies. Inc.).

In aortic vascular smooth muscle cells, angiotensin II causes inflammatory effects that elicit hypertension and atherosclerotic diseases. The effects of angiotensin II are largely attributed to activation of microsomal NADH/NADPH oxidase with production of superoxide anion. MBV suppresses these inflammatory processes via its anti-oxidant properties and anti-inflammatory mechanisms that could include inhibition of NADH/NADPH oxidase. See Cheng et al., Angiotensin II and vascular inflammation, 11(6) Med Sci Monit 194-205 (2005); and Ollinger et al., Bilirubin and biliverdin treatment of atherosclerotic diseases, 6(1) Cell Cycle 39-43 (2007).

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A pharmaceutical composition, comprising:
   a) meso-biliverdin IXα, and
   b) one or more pharmaceutically effective compositions selected from the group consisting of antibiotics, antifungals, antivirals, anti-inflammatories, analgesics, antipyretics, antiseptics, antihistamines, anti-allergy drugs, anaesthetics, and vaccines.

2. The pharmaceutical composition of claim 1, further comprising a pharmaceutically acceptable carrier.

3. A method of treating inflammation in a patient, the method comprising administering to the patient, in an amount effective to reduce inflammation, a pharmaceutical composition comprising:
   a) meso-biliverdin IXα,
   b) an anti-inflammatory drug, and optionally
   c) one or more pharmaceutically effective compositions selected from the group consisting of antibiotics, antifungals, antivirals, analgesics, antipyretics, antiseptics, antihistamines, anti-allergy drugs, anaesthetics, and vaccines.

4. The method of claim 3, wherein the pharmaceutical composition further comprises a pharmaceutically acceptable carrier.

5. The method of claim 3, wherein the inflammation results from a disease type selected from the group consisting of autoimmune diseases, inflammatory diseases, infectious diseases, renal diseases, hepatobiliary diseases, heart diseases, gastrointestinal diseases, respiratory diseases, thyroid diseases, neurodegenerative diseases, venereal diseases, cellular proliferative and/or differentiative diseases, and wounds.

6. The method of claim 3, wherein the inflammation results from diabetes mellitus, type 2 diabetes, cancer, or wounds.

7. The method of claim 3, wherein the inflammation results from type 2 diabetes.

8. The method of claim 3, wherein the inflammation results from wounds.

9. The method of claim 3, wherein the administering comprises a mode of delivery selected from the group consisting of oral delivery, topical delivery, parenteral delivery, intravenous delivery, subcutaneous delivery, intramedullary delivery, intranasal delivery, rectal delivery, and buccal delivery.

10. A method of increasing cell viability in an organ that will be transplanted, the method comprising treating the organ with a therapeutically effective amount of a pharmaceutical composition comprising:
    a) meso-biliverdin IXα, and
    b) one or more pharmaceutically effective compositions selected from the group consisting of antibiotics, antifungals, antivirals, anti-inflammatories, analgesics, antipyretics, antiseptics, antihistamines, anti-allergy drugs, anaesthetics, and vaccines.

11. A method of claim 10, wherein the pharmaceutical composition further comprises a pharmaceutically acceptable carrier.

12. The method of claim 10, further comprising:
    harvesting the organ, and
    transplanting the organ into a patient.

13. The method of claim 10, wherein the organ is treated prior to harvesting.

14. The method of claim 10, wherein the organ is treated after harvesting.

15. The method of claim 10, wherein the organ comprises pancreatic islet cells.

16. The method of claim 15, wherein the pancreatic islet cells are treated with the pharmaceutical composition by infusing the pancreatic islet cells with the pharmaceutical composition through the pancreatic duct of a donor pancreas.

17. The method of claim 15, wherein the pancreatic islet cells are treated with the pharmaceutical composition by incubating the pancreatic islet cells with the pharmaceutical composition.

* * * * *